US006713273B2

(12) United States Patent
Xu et al.

(10) Patent No.: US 6,713,273 B2
(45) Date of Patent: Mar. 30, 2004

(54) HIGH EXPRESSION AND PRODUCTION OF HIGH SPECIFIC ACTIVITY RECOMBINANT S-ADENOSYL HOMOCYSTEINASE (SAHH) AND IMPROVED ASSAYS FOR S-ADENOSYLMETHIONINE (SAM)

(75) Inventors: Mingxu Xu, San Diego, CA (US); Qinghong Han, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 182 days.

(21) Appl. No.: 09/759,990

(22) Filed: Jan. 12, 2001

(65) Prior Publication Data

US 2002/0119491 A1 Aug. 29, 2002

Related U.S. Application Data

(60) Provisional application No. 60/176,444, filed on Jan. 14, 2000.

(51) Int. Cl.[7] .............................. C12Q 1/48; C12Q 1/34

(52) U.S. Cl. .............................................. 435/15; 435/18

(58) Field of Search ............................ 435/15, 18, 232, 435/193, 195

(56) References Cited

U.S. PATENT DOCUMENTS 4,148,888 A 4/1979 Cantoni et al. ............. 424/180
5,998,191 A 12/1999 Tan et al. ................... 435/232

FOREIGN PATENT DOCUMENTS

WO WO 00/63420 10/2000

OTHER PUBLICATIONS

Doskeland and Ueland, Biochem. et Biophys. Acta (1982) 708:185–193.

Fujioka and Takata, J. Biol. Chem. (1981) 256:1631–1635.

Guranowski and Pawelkiewicz, Eur. J. Biochem. (1977) 80:517–523.

Minotto et al., Experimental Parasitology (1998) 90:175–180.

Porcelli et al., Biochim. et Biophys. Acta (1993) 1164:179–188.

Richards et al., J. Biol. Chem. (1978) 253:4476–4480.

Bagnara, A. et al. (1996) *Mol and Biochem Parasitology* 81(1):1–11.

Database EMBL 'Online! Acc.No. U40872, XP002175637 (Dec. 15, 1995), Abstract.

Database SWALL 'Online! Acc.No. P51540, XP002175638 (Oct. 1, 1996), Abstract.

Shimizu, S et al. (1984) *Eur J of Biochemistry* 141(2):385–392.

Ueland, P.M. (1982) *Pharmacological Reviews* 34(3):223–254.

Yeo, E–J. et al. (1999) *J Biol Chem* 274(53):37559–37564.

*Primary Examiner*—Nashaat T. Nashed
(74) *Attorney, Agent, or Firm*—Morrison & Foerster LLP

(57) ABSTRACT

The invention provides novel methods relating to SAM detection and production as well as a novel SAHH enzymatic activity for use in such methods. Additional methods, compositions, and kits relating to the novel SAHH are also provided.

8 Claims, 8 Drawing Sheets

```
99.2% identity in 1461 residues overlap; Score: 1437.0; Gap frequency: 0.0%

SAHH-wild   291 ATGGCTTGCAAATCACCTGCTGGTGCTCCATTCGAGTACAGAATTGCCGACATCAACCTC
A/C,         71 ATGGCTTGCAAATCACCTACTGGTGCTCCATTCGAGTACAGAATTGCCGACATCAACCTC
                ****************** *****************************************

SAHH-wild   351 CATGTTCTCGGCCGTAAGGAACTTACCCTTGCTGAGAAGGAAATGCCAGGTCTTATGGTT
A/C,        131 CATGTTCTCGGCCGTAAGGAACTTACCCTTGCTGAGAAGGAAATGCCAGGTCTTATGGTT
                ************************************************************

SAHH-wild   411 CTTCGTGAGCGTTATTCCGCTTCTAAGCCATTGAAGGGTGTCAGAATCTCTGGTTCCCTC
A/C,        191 CTTCGTGAGCGTTATTCCGCTTCTAAGCCATTGAAGGGTGTCAGAATCTCTGGTTCCCTC
                ************************************************************

SAHH-wild   471 CACATGACAGTCCAGACAGCGGTCCTTATTGAGACACTCACAGCTCTTGGTGCTGATGTC
A/C,        251 CACATGACAGTCCAGACAGCCGTCCTCATCGAGACACTCACAGCTCTTGGTGCTGATGTC
                ******************** ***** ** ******************************

SAHH-wild   531 AGATGGGCTTCCTGCAACATCTTCTCTACACAAGATACAGCCGCTGCTGCTATCGTTGTC
A/C,        311 AGATGGGCTTCCTGCAACATCTTCTCTACACAAGATACAGCCGCTGCTGCTATCGTTGTC
                ************************************************************

SAHH-wild   591 GGCCCAACAGGCACACCAGAGAAGCCAGCCGGTATCCCAGTCTTCGCCTGGAAGGGCGAA
A/C,        371 GGCCCAACAGGCACACCAGAGAAGCCAGCCGGTATCCCAGTCTTCGCCTGGAAGGGCGAA
                ************************************************************

SAHH-wild   651 ACACTCCCAGAATACTGGGAGAACACATACCGCGCTCTCACATGGCCAGATGGTCAAGGC
A/C,        431 ACACTCCCAGAATACTGGGAGAACACATACCGCGCTCTCACATGGCCAGATGGTCAAGGC
                ************************************************************

SAHH-wild   711 CCACAGCAGGTTGTCGATGATGGTGGTGATGCTACACTCCTCATCTCCAAGGGCTTCGAA
A/C,        491 CCACAGCAGGTTGTCGATGATGGTGGTGATGCTACACTCCTCATCTCCAAGGGCTTCGAA
                ************************************************************

SAHH-wild   771 TTCGAAACAGCCGGTGCTGTCCCAGAGCCAACAGAAGCTGACAACCTCGAATACCGCTGC
A/C,        551 TTCGAAACAGCCGGTGCTGTTCCAGAGCCAACAGAAGCTGACAACCTCGAATACCGCTGC
                ******************** ***************************************

SAHH-wild   831 GTTCTTGCTACACTCAAGCAGGTCTTCAACCAAGACAAGAACCACTGGCACACAGTTGCT
A/C,        611 GTTCTTGCTACACTCAAGCAGGTCTTCAACCAAGACAAGAACCACTGGCACACAGTTGCT
                ************************************************************

SAHH-wild   891 GCCGGCATGAACGGTGTTTCCGAAGAGACAACAACAGGTGTCCACCGCCTCTACCAGCTC
A/C,        671 GCCGGCATGAACGGTGTTTCCGAAGAGACAACAACAGGTGTCCACCGCCTCTACCAGCTC
                ************************************************************

SAHH-wild   951 GAGAAGGAGGGCAAACTCCTCTTCCCAGCCATCAACGTCAACGACGCTGTTACAAAGTCC
A/C,        731 GAGAAGGAGGGCAAACTCCTCTTCCCAGCCATCAACGTCAACGACGCTGTTACAAAGTCC
                ************************************************************

SAHH-wild  1011 AAGTTCGATAACATCTACGGCTGTCGCCACTCCCTTATCGATGGTATCAACCGTGCTTCC
A/C,        791 AAGTTCGATAACATCTACGGCTGCCGCCACTCCCTTATCGATGGTATCAACCGTGCTTCC
                *********************** ************************************

SAHH-wild  1071 GATGTCATGATCGGCGGCAAGACAGCTCTCGTCATGGGTTACGGCGATGTCGGGAAGGGC
A/C,        851 GATGTCATGATCGGCGGCAAGACAGCTCTCGTCATGGGTTACGGCGATGTCGGCAAGGGC
                **************************************************** *******

SAHH-wild  1131 TGCGCTCAATCCCTCCGTGGCCAAGGCGCTCGCGTTATCATCACAGAAGTCGACCCTATC
A/C,        911 TGCGCTCAATCCCTCCGTGGCCAAGGCGCTCGCGTTATCATCACAGAAGTCGACCCAATC
                ******************************************************** ***
```

Figure 6a

```
SAHH-wild   1191 TGCGCTCTCCAGGCTGTCATGGAAGGCTACCAGGTCCGCCGCATCGAGGAAGTCGTCAAG
A/C,         971 TGCGCTCTCCAGGCTGCCATGGAAGGCTACCAGGTCCGCCGCATCGAGGAAGTCGTCAAG
                 **************** *******************************************

SAHH-wild   1251 GATGTCGATATCTTCGTTACATGCACAGGAAACTGCGATATCATCTCTGTTGACATGATG
A/C,        1031 GATGTCGATATCTTCGTTACATGCACAGGAAACTGCGATATCATCTCTGTTGACATGATG
                 ************************************************************

SAHH-wild   1311 GCCCAGATGAAGGATAAGGCTATTGTCGGTAACATCGGCCACTTCGATAACGAAATTGAT
A/C,        1091 GCCCAGATGAAGGATAAGGCTATTGTCGGTAACATCGGCCACTTCGATAACGAAATTGAT
                 ************************************************************

SAHH-wild   1371 ACAGATGGCCTCATGAAATACCCAGGCATCAAGCACATCCCAATCAAGCCAGAATACGAC
A/C,        1151 ACAGATGGCCTCATGAAATACCCAGGCATCAAGCACATCCCAATCAAGCCAGAATACGAC
                 ************************************************************

SAHH-wildt  1431 ATGTGGGAATTCCCAGATGGCCACGCTATCCTCCTTCTTGCTGAGGGCCGCCTTCTTAAC
A/C,        1211 ATGTGGGAATTCCCAGATGGCCACGCTATCCTCCTTCTTGCTGAGGGCCGCCTTCTTAAC
                 ************************************************************

SAHH-wild   1491 CTTGGTTGCGCTACAGGTCACCCATCTTTCGTTATGTCAATGTCATTCACAAACCAGACA
A/C,        1271 CTTGGCTGCGCTACAGGTCACCCATCTTTCGTTATGTCAATGTCATTCACAAACCAGACA
                 ***** ******************************************************

SAHH-wild   1551 CTCGCTCAGCTCGACCTCTACGAAAAGAGAGGAAATCTCGAGATGAAGGTTTACACACTT
A/C,        1331 CTCGCTCAGCTCGACCTCTACGAAAAGAGAGGAAATCTCGAGAAGAAGGTTTACACACTT
                 ******************************************* ****************

SAHH-wild   1611 CCGAAGCATCTCGATGAAGAAGTCGTTCGCCTCCACCTCGGATCTCTCGATGTCCACCTT
A/C,        1391 CCGAAGCATCTCGATGAAGAAGTCGCTCGCCTCCACCTCGGATCTCTCGATGTCCACCTT
                 ************************* **********************************

SAHH-wild   1671 ACAAAGCTTACACAGAAGCAGGCTGACTACATCAACGTTCCAGTTGAGGGTCCTTACAAG
A/C,        1451 ACAAAGCTTACACAGAAGCAGGCTGACTACATCAACGTTCCAGTTGAGGGTCCTTACAAG
                 ************************************************************

SAHH-wild   1731 TCTGATGCTTACCGTTATTAA
A/C,        1511 TCTGATGCTTACCGTTATTAA
                 *********************
```

---

```
65.9% identity in 44 residues overlap; Score: 14.0; Gap frequency: 0.0%

SAHH-wild    782 CGGTGCTGTCCCAGAGCCAACAGAAGCTGACAACCTCGAATACC
A/C,         682 CGGTGTTTCCGAAGAGACAACAACAGGTGTCCACCGCCTCTACC
                 ***** *  *  **** *****  ** ** * *** *   ****
```

---

```
80.0% identity in 20 residues overlap; Score: 12.0; Gap frequency: 0.0%

SAHH-wild   1053 GGTATCAACCGTGCTTCCGA
A/C,         674 GGCATGAACGGTGTTTCCGA
                 ** ** *** *** ******
```

Figure 6b

```
87.5% identity in 16 residues overlap; Score: 12.0; Gap frequency: 0.0%

SAHH-wild     564 GATACAGCCGCTGCTG
A/C,          554 GAAACAGCCGGTGCTG
                  ** ******* *****
```

```
64.3% identity in 42 residues overlap; Score: 12.0; Gap frequency: 0.0%

SAHH-wild    1224 GTCCGCCGCATCGAGGAAGTCGTCAAGGATGTCGATATCTTC
A/C,          710 GTCCACCGCCTCTACCAGCTCGAGAAGGAGGGCAAACTCCTC
                  **** **** ** *  *  ***  ***** * * *  ** **
```

```
87.5% identity in 16 residues overlap; Score: 12.0; Gap frequency: 0.0%

SAHH-wild     774 GAAACAGCCGGTGCTG
A/C,          344 GATACAGCCGCTGCTG
                  ** ******* *****
```

Figure 6c

HIGH EXPRESSION AND PRODUCTION OF HIGH SPECIFIC ACTIVITY RECOMBINANT S-ADENOSYL HOMOCYSTEINASE (SAHH) AND IMPROVED ASSAYS FOR S-ADENOSYLMETHIONINE (SAM)

This application claims priority under 35 United States Code § 119(e) from provisional application Ser. No. 60/176,444 filed Jan. 14, 2000, the contents of which are incorporated herein by reference.

TECHNICAL FIELD

The invention relates to a novel recombinant S-adenosyl homocysteinase (SAHH) and methods of using such SAHH. The invention is also directed to diagnostic methods to monitor subjects who have been administered S-adenosylmethionine (SAM), using SAHH. The improved methods of the invention provide rapid and accurate assessment of the concentrations of SAM.

BACKGROUND ART

The administration of S-adenosylmethionine (SAM) as a "nutraceutical" or as a prescribed medication has recently been suggested as an antidepressant, a preventative or therapeutic component in ameliorating liver disease, and a means to diminish the symptoms of arthritis. The mechanism whereby SAM is believed to act is not understood completely, but it is believed that the relative concentrations of SAM and homocysteine, which is a metabolic product of SAM, affect methylation levels which, in turn, have profound physiological effects. In view of the importance of this drug, it would be desirable to have a reliable and easily performed method to monitor the concentration of the administered pharmaceutical. The present invention provides an improved method to assess therapeutic levels of SAM in subjects administered this drug using S-adenosyl homocysteinase (SAHH). The present invention is also directed to a recombinantly produced SAHH that differs from the previously reported SAHH.

S-adenosylhomocysteinase (S-adenosylhomocysteine hydrolase; SAHH, EC 3.3.1.1) catalyses the reversible conversion of SAH to homocysteine and adenosine (de la Haba and Cantoni, 1959). Various structural analogues of adenosine inactivate SAHH from a number of organisms, resulting in cytotoxicity (Ueland, 1982). Inhibition of SAHH activity by the nucleoside analogues depends on the inhibitor structure as well as the source of the enzyme. SAHH was initially cloned from the *Trichomonas vaginalis* gene and previously characterized (Bagnara et al., 1996).

Minotto, L., Ko, G. -A., Edwards, M. R., and Bagnara, A. S. [*Trichomonas vaginalis* Expression and characterization of recombinant S-adenosylhomocysteinase. *Experimental Parasitology* 90, 175–180, 1998] have further characterized the *T. vaginalis* SAHH. The gene encoding S-adenosylhomocysteinase in *Trichomonas vaginalis* was expressed on pQE-30 in *Escherichia coli* to facilitate the characterization of the enzyme.

A 6× His N-terminal tag expression system (QIAGEN) enabled one-step purification of six mg of rSAHH, obtained from a 100-ml bacterial culture by affinity chromatography using a nickel-NTA matrix. The recombinant enzyme was found to have molecular weight of approximately 56,000. Properties of rSAHH include a similar apparent Km for adenosine of 20–25 μM for the recombinant and similar inhibition/inactivation patterns adenosine analogues such as arabinosyl adenine (ara-A).

The results of Minotto et al., 1998, differ from the finding of others who have shown that the hydrolase can exist in various oligomeric forms depending on the source of the enzyme. The SAHH activity from prokaryotes is as a hexamer (Shimizu et al., 1984) or tetramer (Porcelli et al., *Biochim. et Biophys. Acta,* 1164, 179–188, 1993). The enzyme from rat liver (Fujioka and Takata, *J Biol. Chem.,* 256, 1631–1635, 1981), calf liver (Richards et al., *J. Biol. Chem.,* 253, 4476–4480, 1978), and other animal sources (Doskeland and Ueland, *Biochem et Biophys Acta* 708, 185–193, 1982) is tetrameric but with uncertainty whether the subunits are identical or similar. SAHH from a plant source is functional as a homodimer (Guranowski and Pawelkiewicz, Eur. *J. Biochem.* 80, 517–523, 1977). This is the first report of an SAHH activity being functional in the monomeric form (Minotto et al., 1998).

DISCLOSURE OF THE INVENTION

The present invention relates to an improved and novel method for analyzing SAM levels in a sample. In one aspect of the invention, this method may be used to assay therapeutic levels of SAM in a sample from a subject such as, but not limited to, a patient being administered this compound. The method may also be used, to assay SAM levels in a biological fluid such as, but not limited to, blood or other biological fluids of a subject. Such methods may be conducted in vivo, such as in the bloodstream, or in vitro, such as with a sample taken from a subject. The methods may be used as part of a diagnostic protocol or as part of a therapeutic protocol. As part of a therapeutic protocol, the methods may serve in part to monitor the conditions or progress of the therapy.

In one embodiment of the invention, the assay method may be performed by contacting a sample with glycine N-methyltransferase (GMT), glycine, and SAHH activity. Determination of SAM levels in the sample may then be made by measuring one or more reaction products in the sample, wherein the amount of reaction product(s) is directly proportional to SAM levels in the sample. In one embodiment of the invention, the reaction product homocysteine (HC) is measured directly or indirectly. Indirect measurements of HC may be made by any means including, but not limited to, treatment with homocysteinase (HCYase) and measuring the levels of one or more reaction products (e.g. alpha keto glutarate, $H_2S$, or $NH_3$). The $H_2S$ reaction product may be measured directly or indirectly by measuring absorbance or fluorescence. One means of measuring fluorescence is by use of a fluorescence generating reagent.

The invention also provides a novel SAHH, nucleic acids that encode it, compositions comprising it, and methods for its preparation and use. The SAHH contains an amino acid sequence encoded by SEQ ID NO:1. Nucleic acids which encode the SAHH of the invention may be placed in any appropriate nucleic acid vector for propagation, amplification or expression. The nucleic acids may also be operably linked to other nucleic acids to permit the expression of the SAHH covalently linked to one or more additional amino acids. The additional amino acids result in the production of a hybrid or chimeric protein comprising SAHH. In one preferred embodiment of the invention, the additional amino acids are those of a histidine tag (His tag) which improves subsequent purification of the SAHH of the invention.

The nucleic acids of the invention may be introduced into any appropriate host cell or organism, such as, but not limited to, bacteria, fungi, and higher eukaryotic cells. These cells may be used to recombinantly express the nucleic acids of the invention, optionally followed by isolation and/or purification of the expressed protein. Alternatively, the nucleic acids may also be expressed by use of in vitro expression systems.

Purification of the SAHH of the invention may be by any convenient or appropriate means such as, but not limited to, precipitation and/or chromatography. In a preferred embodiment of the invention, the purification is performed in whole or in part by affinity chromatography based on interaction with a His tag. In another preferred embodiment of the invention, the SAHH is purified such that it appears as a single band when analyzed by SDS polyacrylamide gel electrophoresis.

The SAHH of the invention may also be formulated into compositions, such as those comprising pharmaceutical agents or excipients. The SAHH may also be used in the methods of the invention, such as the assay methods described above, as well as additional methods such as that for assaying homocysteine to SAH conversion in a sample to measure homocysteine levels. In another aspect of the invention, the SAHH may be used in methods of depleting excess homocysteine in a sample in vivo or in vitro by conversion to SAH. Of course the samples of the invention may be any biological fluid of interest.

BRIEF DESCRIPTION OF THE DRAWINGS

FIGS. 6*a–c* is an alignment of the nucleotide sequence of SAHH of the invention (SEQ ID NO:1) with the wild type sequence (SEQ ID NO:6).

MODES OF CARRYING OUT THE INVENTION

Figure 1:
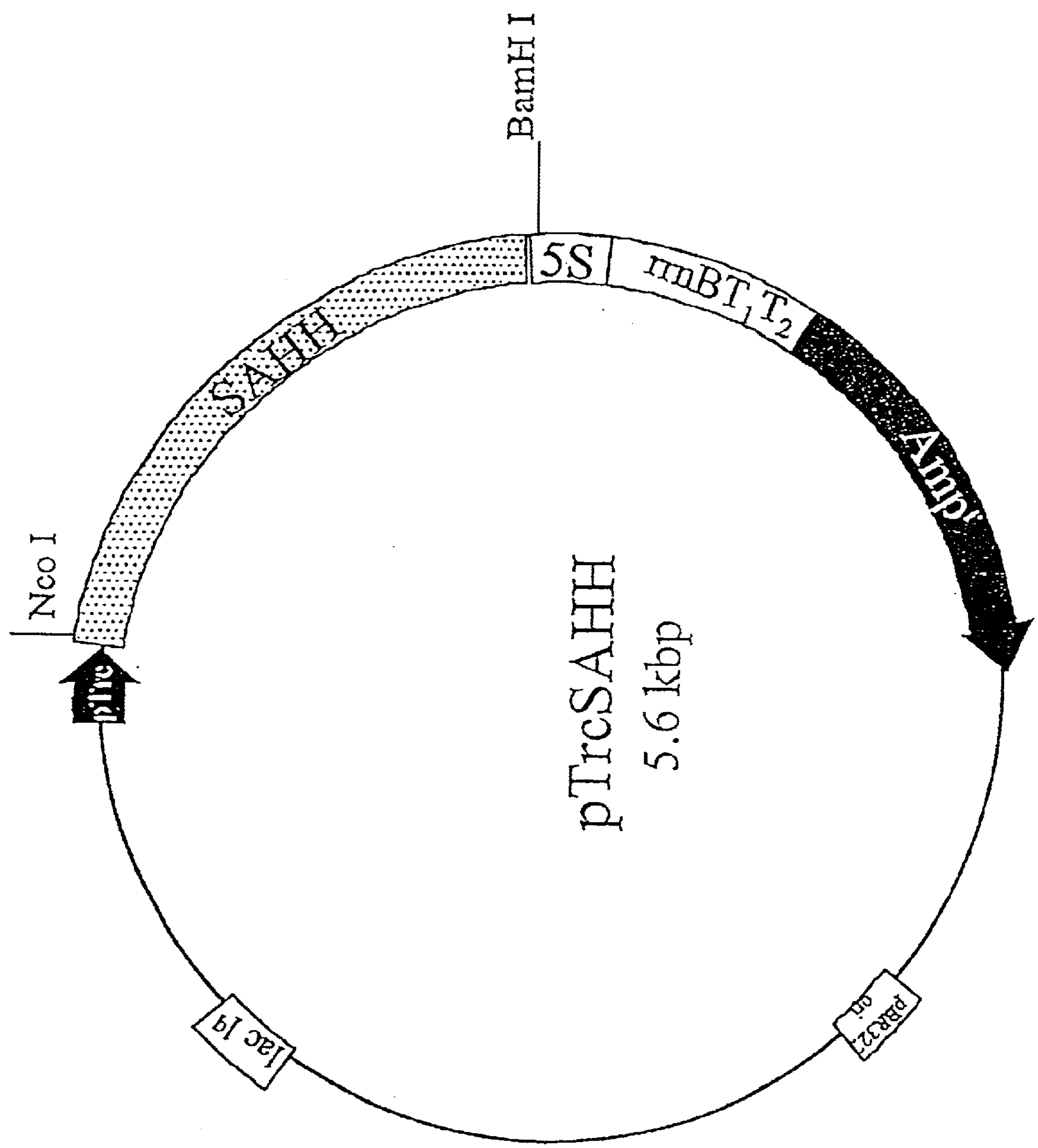
FIG. 1 depicts the pTrcSAHH as inserted to pTrc multiclone site NcoI and BamHI.

The invention provides an isolated and recombinant nucleic acid encoding SAHH comprising SEQ ID NO:1, as well as the corresponding SAHH amino acid sequence (SEQ ID NO:7). In another aspect, the SAHH gene is modified to encode a modified His•SAHH, which has an extra six histidines, in the N-terminal of the SAHH gene.

In another aspect of the invention, the invention provides methods for the propagation and maintenance of the nucleic acids and their use in the expression of SAHH proteins. The invention further provides methods for the purification of SAHH by single or two step purification methods.

The invention is directed, in one embodiment, to the measurement of SAM in biological fluids. As used herein, a "biological sample" refers to a sample of tissue or fluid isolated from an individual, including but not limited to, for example, blood and blood fractions, plasma, serum, cerebral spinal fluid, lymph fluid, urine, the external sections of the skin, respiratory, intestinal, and genitourinary tracts, body secretions, tears, saliva, milk, lymphatic or other extracts taken from an animal, cells (including but not limited to blood cells), tumors, organs, and also samples of in vitro cell culture constituents. Measurement in plasma or serum is preferred.

As used herein, "expression" includes transcription and/or translation.

As used herein, the term "comprising" and its cognates are used in their inclusive sense; that is, equivalent to the term "including" and its corresponding cognates.

Unless defined otherwise all technical and scientific terms used herein have the same meaning as commonly understood to one of ordinary skill in the art to which this invention belongs.

SAHH is the enzyme responsible for the conversion to homocysteine from S-adenosyl homocysteine (SAH), which ultimately lowers the level of SAM. Since the levels of SAM administered for therapeutic purposes are very high in proportion to endogenous levels either of SAH or homocysteine (HC), the following scheme can be used to assay for SAM levels in subjects being administered this compound. This assay thus serves as a drug monitoring device, which can be in the form of a kit. The outline of the assay is shown in the scheme below.

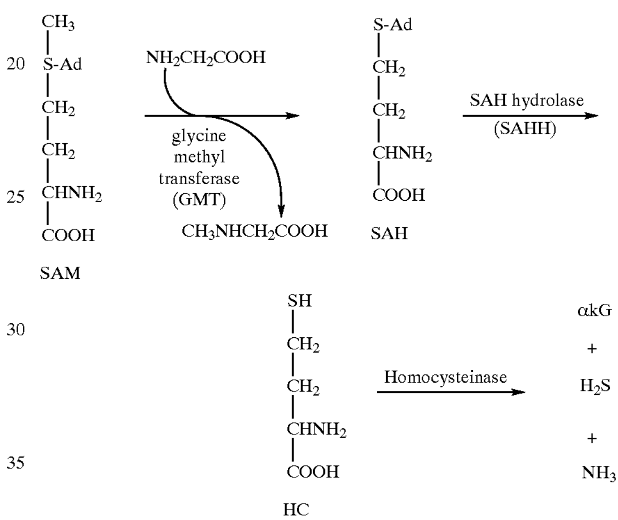

As described herein, this general approach to assaying SAM is improved by efficient production of SAHH or His•SAHH and by selection of a homocysteinase which has a high specificity for homocysteine. Although the levels of homocysteine are small relative to those of SAM, thus assuring that the estimate of SAM is not appreciatively distorted by endogenous SAH or HC, the presence of cysteine in bodily fluids at levels significantly higher than the levels of the homocysteine may result in interference if an enzyme of insufficient specificity is used. The end-product measured in the method of the invention is hydrogen sulfide in the presence of a fluorescence-generating reagent.

The SAHH also catalyzes the reverse reaction of the conversion of homocysteine to SAH, ultimately elevating the level of SAM. Such a reaction is useful in another type of assay, an enzyme-conversion immunoassay of homocysteine, in which homocysteine is measured. Specifically, the SAHH or His•SAHH of the invention is used to quantitatively convert homocysteine to SAH and then the end-product, SAH, is then measured using a standard ELISA assay. This can be performed by providing a sufficient or higher (even excess) amount of SAH. Alternatively, a fluorescent antibody to SAH can be used for quantitation of the resulting SAH. Such an immunoassay can be used as a kit and can be useful for measuring plasma homocysteine, for example, in a range of approximately 1–100 $\mu$M.

SAHH or His•SAHH of the invention can also be used as a reagent, in particular for screening for inhibitors and inactivators of the enzyme for use as reagents themselves and as potential therapeutics, for example, in cancer, malaria, arthritis, and other diseases. The SAHH reagent preferably is in the form of a kit that contains an assay, which is simple due to coupling with homocysteine and measurement of the resulting hydrogen sulfide with a dialkyl phenylene diamine reagent such as DBPDA.

Other uses of recombinant SAHH include a therapeutic cancer gene for combination with SAH analogs, which would act as enzyme activated prodrugs with toxicity provided by toxic adenosine analogs released by SAHH. Such adenosine analogs would not be toxic when conjugated to HCY as an SAH analog. Analogs of homocysteine could also be used, such as selenohomocysteine conjugated with adenosine or an adenosine analog, which in combination with SAHH and rMETase gene therapy would release the very toxic hydrogen selenol as well as the toxic adenosine analog in cancer cells transduced with the two genes.

A preferred embodiment includes a kit for assaying a sample. Preferably, a kit contains instructions for performing the assay, which instructions may be printed on a package insert, packaging or label included in the kit. The printed matter can also be included on receptacles included in the kit, and indicia of sample and reagent volumes can be indicated in the test receptacle. The precise instructions would vary depending upon the substance to be detected and/or detection method used, but may include instructions for one or more of the following: instructions for dilution of the kit components and/or the sample if necessary, directions for volume or concentration of enzyme used for each assay, volume of sample to add to the assay, directions for adding fluorescence-generating reagents, directions for taking measurement of products, preferred temperature conditions, and timing of component addition and mixing, and use of a standard to calibrate test results.

Production of the SAHH of the invention may be performed by any conventional means. By way of example, and without limiting the scope of the invention, an appropriate vector encoding a SAHH of the invention may be used to first transform bacteria used to express the enzyme. The transformed bacteria can then be cultivated (fermented) in liquid culture for a number of hours until they reach a high density. If the SAHH encoding sequence is under the control of an inducible promoter, the appropriate inducer may be added. After cultivation, the cells may then be harvested by centrifugation and stored frozen until used.

Frozen cells may be thawed and lysed prior to the addition of components to precipitate cell debris. The debris may be collected by centrifugation and the supernatant containing SAHH activity collected. The supernatant can be diluted with an appropriate buffer prior to loading on a prepared chromatographic column. The SAHH may be eluted by a gradient, or more preferably by single step elution in a small volume. The SAHH can then be formulated into a storage preparation prior to use.

In addition to the single step purification protocol provided above, His tag containing SAHH may be purified by affinity chromatography. By way of example and without limiting the invention, bacterial cells expressing His tag SAHH may be cultivated and harvested as described above. The frozen cells may then be thawed and disrupted as described above to prepare a cell suspension. Solid ammonium sulfate may then be added to the suspension and the mixture kept on ice followed by centrifugation. The supernatant containing SAHH activity is then collected and applied to a previously prepared (equilibrated) Ni-NAT chromatography media. The column is then washed and then developed with a single step elution. Active fractions may be pooled and dialyzed prior to formulation into conditions for frozen storage.

As illustrated in the following examples, SAHH encoding sequences were cloned from *Trichomonas vaginalis* and expressed in *E. coli* according to the procedures described below. The nucleotide sequence for the gene encoding SAHH is provided herein, along with a comparison of the wild type sequence, which is equivalent to the sequence disclosed in Minotto et al., 1998, as shown in FIGS. 6*a–c*. A comparison of the two sequences reveals eleven point mutations, which are listed below in Table 1.

TABLE I

COMPARISON OF SAHH SEQUENCES

| | Wild type | A/C's | Change of amino acid |
|---|---|---|---|
| There are 11 point mutations. | | | |
| No. 19 | (G)CT | (A)CT | Ala. → Thr. |
| No. 201 | GC(G) | GC(C) | |
| No. 207 | CT(T) | CT(C) | |
| No. 210 | AT(T) | AT(C) | |
| No. 501 | GT(C) | GT(T) | |
| No. 744 | GT(G) | TG(C) | |
| No. 834 | GG(G) | GG(C) | |
| No. 897 | CC(T) | CC(A) | |
| No. 917 | G(T)C | G(C)C | Val. → Ala. |
| No. 1314 | GA(T) | GA(A) | Asp. → Glu. |
| No. 1346 | G(T)T | G(C)T | Val. → Ala. |

Figure 2:
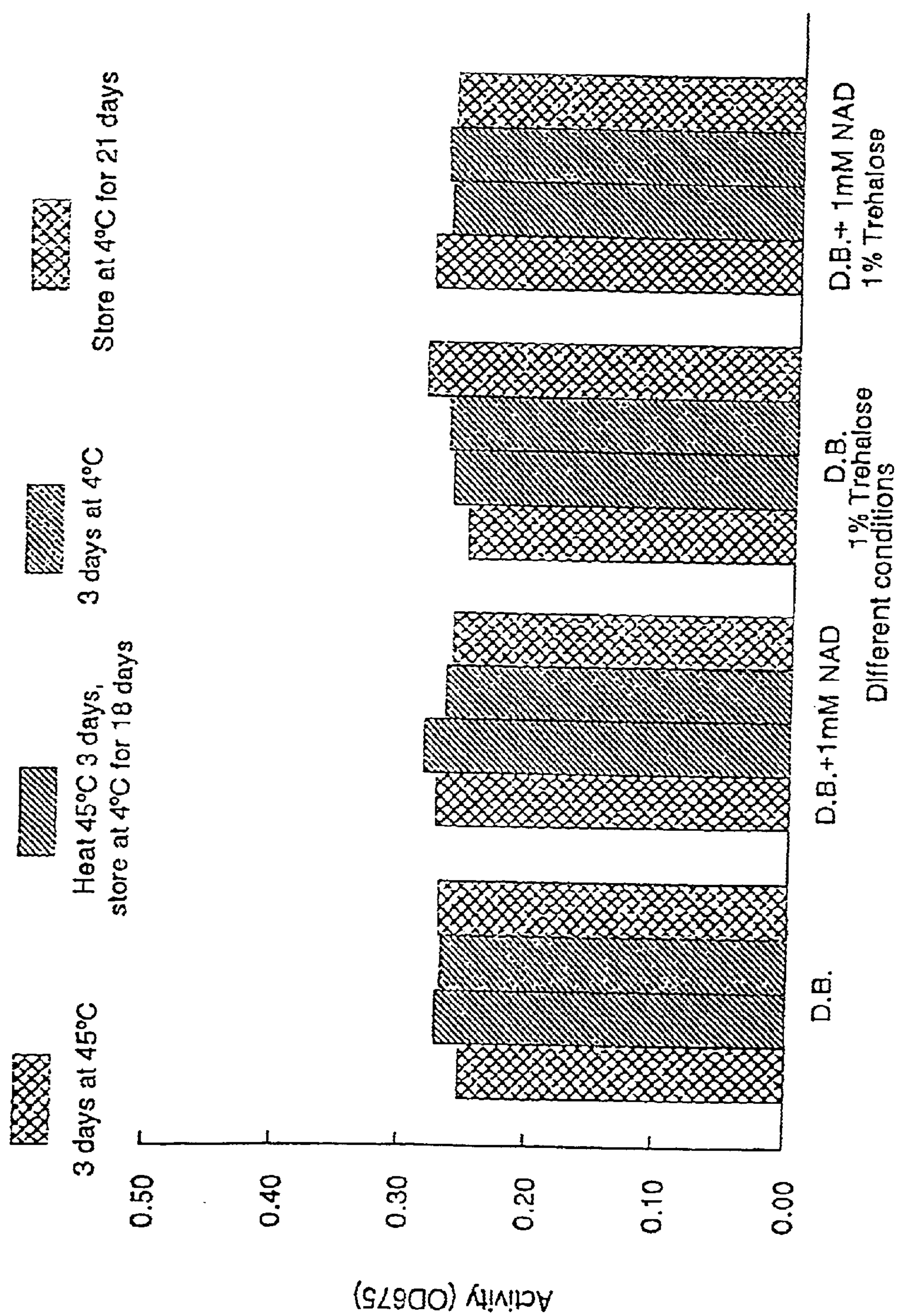
FIG. 2 contains the results of a stability study of SAHH.
Figure 3:
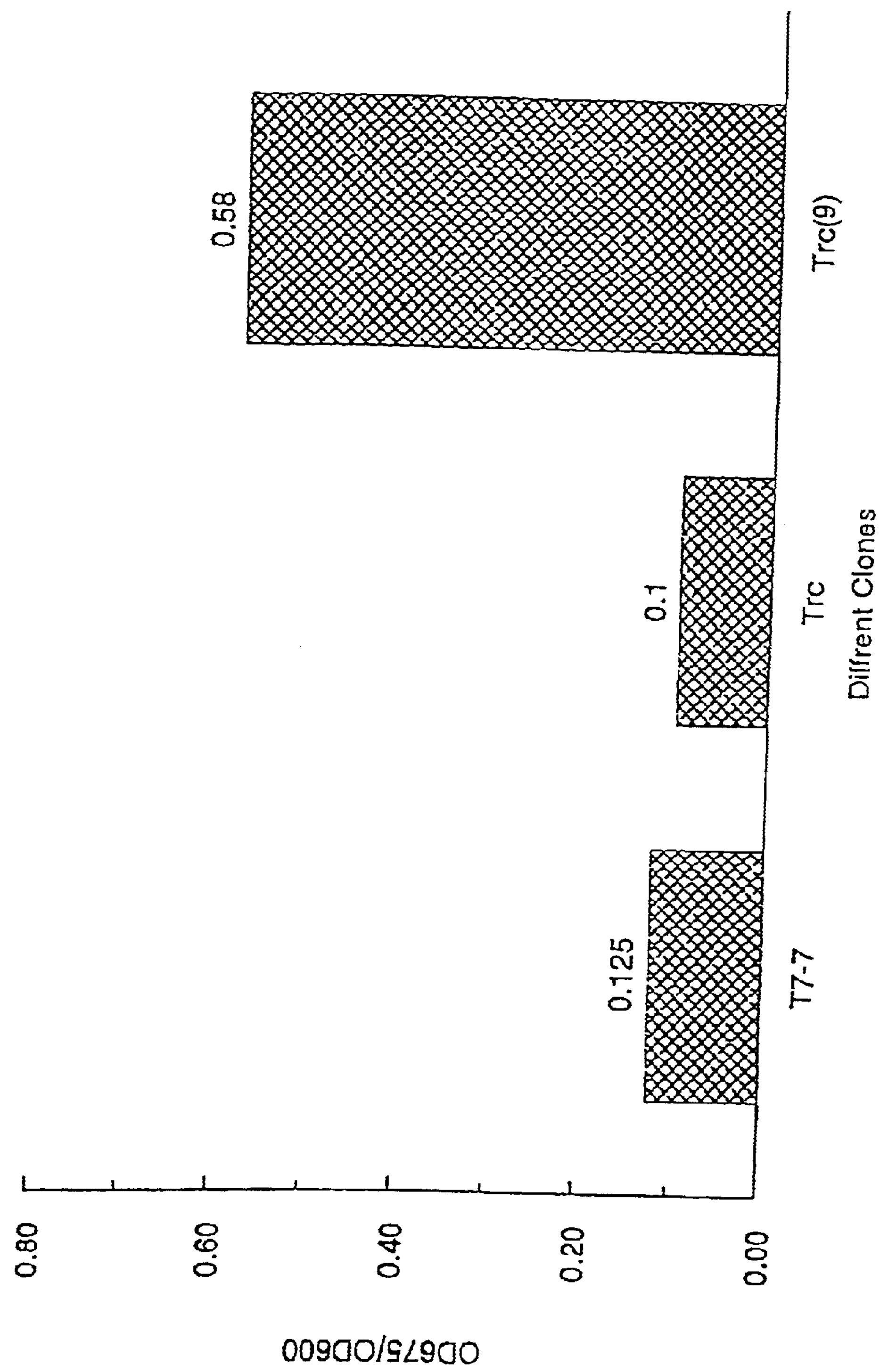
FIG. 3 shows screening clones of SAHH.
Figure 4:
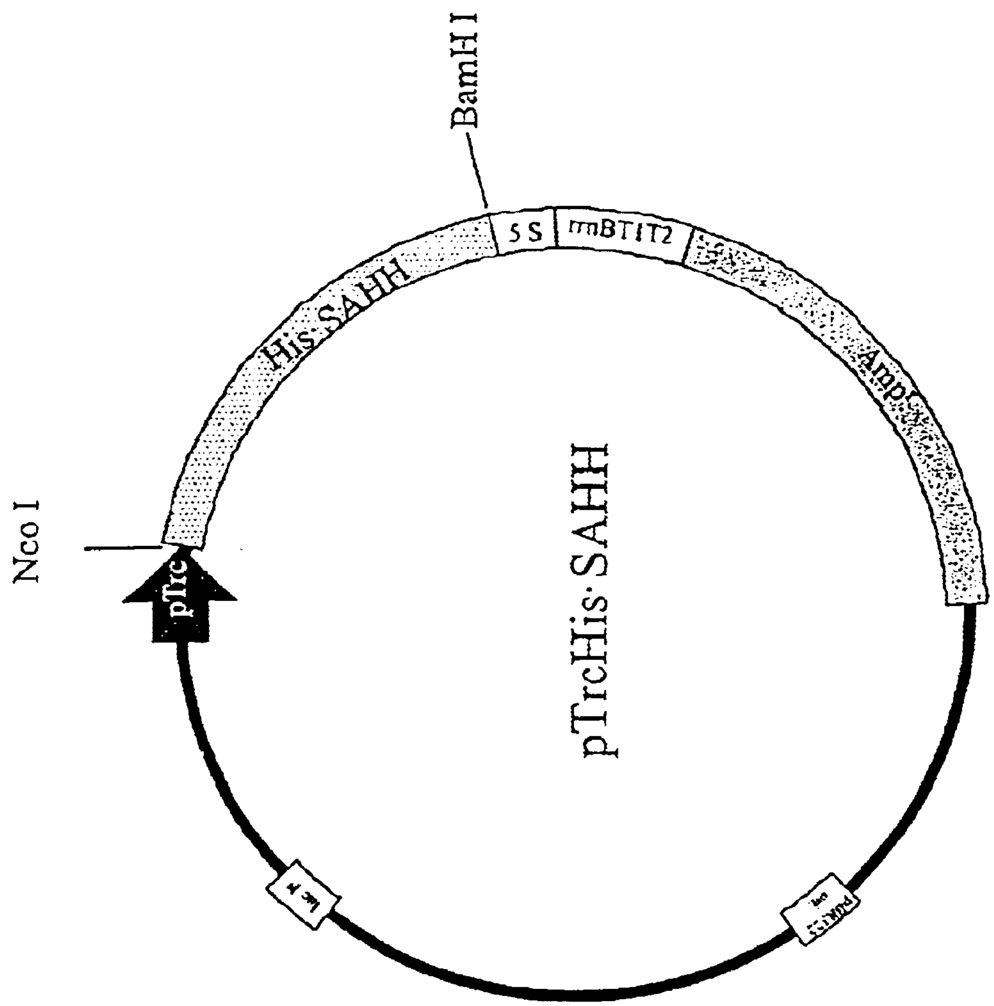
FIG. 4 depicts the pTrcHis•SAHH as inserted to pTrc multicloning site NcoI and BamHI.
Figure 5:
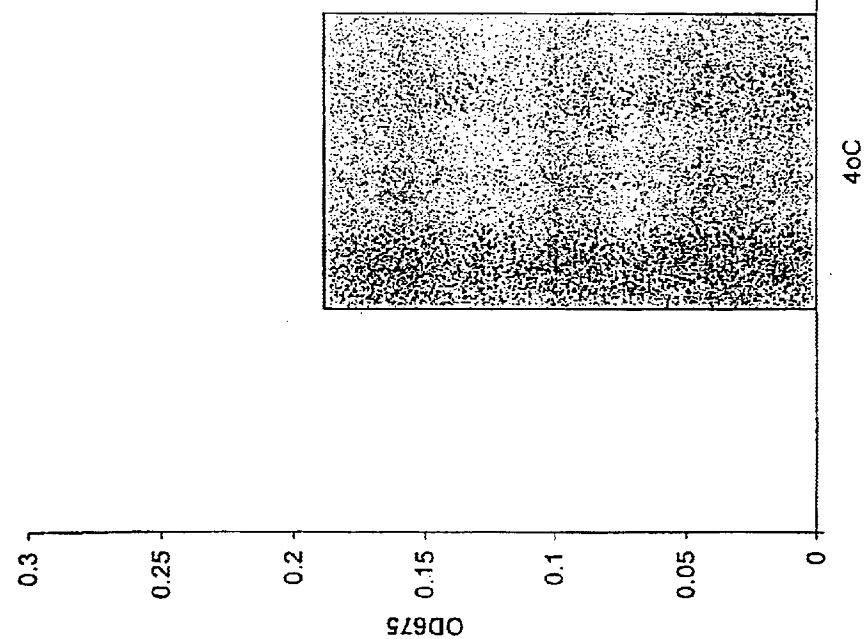
FIG. 5 contains the results of a stability study of His•SAHH.

The SAHH enzyme of the invention has favorable properties. For instance, the SAHH has a high specific activity of at least 1.5 U/ml. Further, the cloned SAHH of the invention provides a high expression of 20% of total cell protein. Moreover, SAHH produced according to the method of the invention has high stability as illustrated in the attached FIGS. 2 and 5. For example, SAHH and SAHH•His is stable at 45° for three days without activity loss as illustrated in FIGS. 2 and 5 respectively.

The following example is intended to illustrate but not to limit the invention.

EXAMPLE 1

Cloning of the SAHH Gene into the pQE-30 Expression Vector

The genomic sequence encoding SAHH in *T. vaginalis* (Bagnara et al, 1996) was amplified by PCR using oligonucleotide primers containing engineered restriction enzyme sites for BamHI and Pst1 in the upstream (sense) and downstream (antisense) primers, respectively (restriction sites are underlined in both cases): upstream primer,

```
                                    (SEQ ID NO:2)
5' TTTTGGATCCGCTTGCAAATCACCTGCTGGTGC 3';
```

downstream primer,

```
                          (SEQ ID NO:3)
3' CTGCTATCGAGGGGGACGTCTTTT 5'.
```

The recombinant expression vector pQE-30 was transformed into the *Eseherichia coli* host strain M15[pREP4] (Villarejo and Zabin, 1974) (QIAGEN).

EXAMPLE 2

Expression, Purification, and Analysis of Recombinant SAHH

Clones containing the pQE-30-SAHH construct were grown overnight in *E. coli* M15 with ampicillin (100 $\mu$g/ml)

and kanamycin (25 μg/ml). Expression was induced with 0.1 mM IPTG, followed by growth at 39° C. for 14 h with vigorous shaking. Harvested cells were disrupted by sonication in 50 mM Na-phosphate, pH 8.0, 300 mM NaCl followed by centrifugation at 12,000 g for 20 min. The recombinant enzyme was then isolated by differential elution from the Ni-NTA column with 50 mM Na-phosphate, pH 6.0, 300 mM NaCl, 10% glycerol containing various concentrations of imidazole. Aliquots of the purified recombinant enzyme were stored at 4° C. without additional glycerol) while other aliquots were mixed with glycerol (50% final concentration) for storage at −20 and −79° C. to determine the effect of storage on enzyme activity. The size of the active recombinant enzyme was also analyzed under nondenaturing conditions using size-exclusion capillary chromatography (Superdex 200 PC column) on a Pharmacia Biotech SMART chromatography system.

EXAMPLE 3

Expression of SAHH in *E. coli*

The expression of the SAHH gene has been achieved in *E. coli*, a host which provides an SAHH-negative background (Shimizu et al., *Eur. J. Biochem.,* 141, 385–392, 1984). The *E. coli* clones containing the recombinant SAHH gene sequence exhibited a high degree of expression of the enzyme but largely as insoluble “inclusion bodies” when induced at 37° C. with 1–2 mM IPTG. Lowering the temperature to 30° C. and decreasing the concentration of IPTG to 0.1 mM decreased the level of expression and resulted in a greater proportion of the enzyme being expressed in a soluble and active form. The recombinant SAHH comprised approximately 12% of the total soluble protein.

EXAMPLE 4

Purification and Characterization of the Recombinant Protein

The recombinant SAHH was purified by affinity chromatography on an NI-NTA column. The molecular weight of the enzyme was an apparent 55,000–56,000 (FIG. 1). The results of the size-exclusion chromatography using a Superdex 200 PC capillary column indicated that the molecular weight of the recombinant enzyme was about 55,000 under nondenaturing conditions. The enzyme is active under these conditions and that SDS-PAGE demonstrated subunit molecular weight of approximately 55,000–56,000, these data indicate that the *T. vaginalis* enzyme is functional as the monomer. This result differs from the findings of others who have shown that the hydrolase can exist in oligomeric form, with the quaternary structure depending on the source of the enzyme.

EXAMPLE 5

Fermentation and Purification of S-adenosyl-L-homocysteine Hydrolase

Fermentation:

1. 10 μl of bacteria from mast cell bank were inoculated to 5 ml L.B. and cultivated with shaking at 37° C. for 6 hours.
2. 0.5 ml of bacteria from step 1 were transferred to 3 bottles of 400 ml L.B. and cultivated with shaking at 37° C. overnight.
3. The cells were collected by centrifuging at 3000 rpm at 4° C., suspended in L.B., and seeded to ferment.
4. Cells were cultivated at fermentor for approximately 6 hours at 28° C. until cell density reaches OD600 7.
5. The cells were induced by adding 0.1 mM IPTG and cultivated at 28° C. overnight.
6. The cells were harvested by centrifuging at 4000 rpm at 4° C. and stored at −80° C. until purification.

Purification:

1. The cells were lysed by pass through the homogenizer three times.
2. The cell lysis was mixed with 2% PEI, 30% alcohol, and 8% PEG and heated in waterbath until temperature reached 37° C.
3. Cell debris was discarded by centrifuging at 15,000 rpm for 30 minutes and the supernatant was collected.
4. The supernatant was diluted two-fold by adding 20 mM potassium phosphate buffer pH 8.3, 1 mM DTT and EDTA.
5. The supernatant was loaded to pre-equilibrium DEAE-Sepharose fast flow column.
6. The column was prewashed with 20 mM potassium phosphate buffer pH 7.6, 40 mM NaCl, 1 mM DTT and 1 mM EDTA until OD280 reached less than 0.2.
7. SAHH was eluted by 20 mM potassium phosphate buffer pH 7.6, 100 mM NaCl, 1 mM DTT and EDTA.
8. Final product was formulated by adding 30% glycerol and 1 mM NAD to the SAHH elution.

Specificity

High expression clone expressed SAHH 20% of total protein. After purification, the specific activity of SAHH was 1.64 units/mg protein. The purity reached over 90%.

Stability

The enzyme was formulated as follows: 20 mM potassium phosphate buffer, pH 7.6, 100 mM sodium chloride, 30% glycerol, 1 mM DTT, 1 mM NAD, and 1 mM EDTA. See FIG. 2.

EXAMPLE 6

SAHH Activity Measurement

Reagent:

Assay buffer: 20 mM potassium phosphate, pH 8.0, 1 mM DTT, and 1 mM EDTA.

2 mM S-adenosyl-L-homocysteine (SAH)

rHCYase (5 mg/ml)

L-homocysteine (various concentrations)

40 mM DBPDA, dissolved in 6 M HCl 40 mM potassium ferricyanide

Assay Procedure:

| | Blank | Standard curve | Test |
|---|---|---|---|
| Assay buffer (μl) | 940 | 970 | 920 |
| rHCYase (μl) | 10 | 10 | 10 |
| L-homocysteine (μl) | — | 20 | — |
| SAH (μl) | 50 | — | 50 |
| Sample (μl) | — | — | 20 |
| Mix well and incubate at 37° C. for 5 min. | | | |
| DBPDA (μl) | 50 | 50 | 50 |
| Potassium ferricyanide (μl) | 50 | 50 | 50 |

Mix well and incubate at 37° C. for 10 min. and read absorbance at 675 nm or fluorescence at EX665 nm/EM690 nm. 1 unit is defined as 1 μmole of S-adenosylhomocysteine hydrolated in 1 min. at 37° C. in the presence of excess rHCYase.

EXAMPLE 7 rSAHH•His Tag Preparation

To construct the expression vector, the SAHH gene was modified by PCR. The 5' primer is

```
                                  (SEQ ID NO:4)
CATCATCATCATCATCACGCTTGCAAATCACCTACTGG
    6 × His·Tag
```

and the 3' primer is

```
                         (SEQ ID NO:5)
ATGCATGGATCCTTAATAACGGTAAGCATC.
      BamHI
```

The pTrc 99A(Pharmacia Biotech) was employed as a expression vector. The modified His•SAHH which has extra six histidine codes in N-terminal of SAHH gene was inserted into Nco I-blunt and BamH I site. *E coli* JM109 was employed as the host strain for His•SAHH expression.

EXAMPLE 8

Purification of Recombinant S-Adenosylhomocysteine Hydrolase with His-tag

Cell Disruption:

500 grams of frozen cells (−80° C.) of *E. coli* in which SAHH was expressed were thawed and suspension in 500 ml 20 mM potassium phosphate buffer pH 7.6 containing 1 mM DTT and 1 mM EDTA. Disruption of cells with homogenizer (HC-8000, Microfluidics International Corporation) at 5,000 psi for three times.

Ammonium Sulfate Precipitation:

Crystalline ammonium sulfate (20% w/v) was added to disrupted cell suspension. After mixture on ice for 20 minutes, the preparation was centrifuged at 12,000 rpm, 4° C. for 30 minutes, then collected the supernatant for further purification.

Ni-NAT Superflow Chromatography:

The clear supernatant containing 10 mM imidazole was applied to Ni-NAT Superflow column (2.0×20 cm) equilibrated with Binding Buffer (50 mM potassium phosphate pH 7.6, 0.5 M NaCl, 10 mM imidazole, 1 mM EDTA and 0.01% α-mercaptoethanol). The column was washed with 3 bed vol. Binding Buffer until the absorbance at 280 nm reached the baseline, then washed with Wash Buffer (50 mM potassium phosphate pH 7.6, 0.5 M NaCl, 50 mM imidazole, 1 mM EDTA and 0.01% α-mercaptoethanol) until the absorbance at 280 nm reached the baseline. The enzyme was eluted Elute Buffer (50 mM potassium phosphate pH 7.6, 0.5 M NaCl, 300 mM imidazole, 1 mM EDTA and 1 mM DTT). Active fractions were pooled, and dialyzed against 50 vol of 20 mM potassium phosphate pH 7.6 containing 1 mM DTT and 1 mM EDTA. The final product with 30% glycerol and 1 mM NAD was stored at −80° C.

The recombinant SAHase was purified by a two-step procedure, ammonium sulfate and affinity chromatography, which is particularly fast and efficient. The purified preparation gave a single band by SDS-polyacrylamide gel electrophoresis. The specific activity of purified rSAHase is 1.79 units/mg protein according to the above method.

What is claimed is:

1. A method to assess therapeutic levels of S-adenosylmethionine (SAM) in a biological fluid sample which method comprises providing said sample with an effective amount of glycine N-methyltransferase (GMT), an effective amount of a S-adenosyl homocysteine hydrolase (SAHH) or His•SAHH (N-terminal histidine tagged SAHH), and glycine; and measuring one or more reaction products in said sample wherein the level(s) of said one or more reaction products is directly proportional to the level of SAM in the sample.

2. The method of claim 1 wherein the product detected is homocysteine (HC).

3. The method of claim 2 wherein said HC is measured by a method which comprises treating the sample with homocysteinase (HCYase) and measuring the concentration of at least one product obtained by the reaction of HCYase with said homocysteine.

4. The method of claim 3 wherein the product measured is $H_2S$.

5. The method of claim 4 wherein said $H_2S$ is measured by fluorescence or is measured by absorbance.

6. The method of claim 1, wherein the SAHH comprises an amino acid sequence encoded by SEQ ID NO:1.

7. A kit for assaying a sample containing S-adenosylmethionine (SAM), the kit comprising S-adenosyl homocysteine hydrolase SAHH or His•SAHH (N-terminal histidine tagged SAHH), N-methyltransferase (GMT), glycine and instructions for use.

8. A method for determining S-adenosylmethionine SAM concentration comprising:

a biological sample containing SAM; and an effective amount of glycine N-methyltransferase (GMT), glycine, and S-adenosyl homocysteine hydrolase (SAHH) or N-terminal histadine tagged SAHH (His•SAHH), wherein SAHH or His•SAHH activity results in a product that is capable of being measured to determine the amount of SAM in the sample.

* * * * *

SEQUENCE LISTING

```
<160> NUMBER OF SEQ ID NOS: 7

<210> SEQ ID NO 1
<211> LENGTH: 1461
<212> TYPE: DNA
<213> ORGANISM: Homo sapiens (nucleotide sequence of SAHH)

<400> SEQUENCE: 1

atggcttgca aatcacctac tggtgctcca ttcgagtaca gaattgccga catcaacctc      60

catgttctcg gccgtaagga acttaccctt gctgagaagg aaatgccagg tcttatggtt     120

cttcgtgagc gttattccgc ttctaagcca ttgaagggtg tcagaatctc tggttccctc     180

cacatgacag tccagacagc cgtcctcatc gagacactca cagctcttgg tgctgatgtc     240

agatgggctt cctgcaacat cttctctaca caagatacag ccgctgctgc tatcgttgtc     300

ggcccaacag gcacaccaga gaagccagcc ggtatcccag tcttcgcctg gaagggcgaa     360

acactcccag aatactggga gaacacatac cgcgctctca catggccaga tggtcaaggc     420

ccacagcagg ttgtcgatga tggtggtgat gctacactcc tcatctccaa gggcttcgaa     480

ttcgaaacag ccggtgctgt tccagagcca acagaagctg acaacctcga ataccgctgc     540

gttcttgcta cactcaagca ggtcttcaac caagacaaga accactggca cacagttgct     600

gccggcatga acggtgtttc cgaagagaca acaacaggtg tccaccgcct ctaccagctc     660

gagaaggagg gcaaactcct cttcccagcc atcaacgtca acgacgctgt tacaaagtcc     720

aagttcgata acatctacgg ctgccgccac tcccttatcg atggtatcaa ccgtgcttcc     780

gatgtcatga tcggcggcaa gacagctctc gtcatgggtt acggcgatgt cggcaagggc     840

tgcgctcaat ccctccgtgg ccaaggcgct cgcgttatca tcacagaact cgacccaatc     900
```

-continued

```
tgcgctctcc aggctgccat ggaaggctac caggtccgcc gcatcgagga agtcgtcaag    960

gatgtcgata tcttcgttac atgcacagga aactgcgata tcatctctgt tgacatgatg   1020

gcccagatga aggataaggc tattgtcggt aacatcggcc acttcgataa cgaaattgat   1080

acagatggcc tcatgaaata cccaggcatc aagcacatcc caatcaagcc agaatacgac   1140

atgtgggaat tcccagatgg ccacgctatc ctccttcttg ctgagggccg ccttcttaac   1200

cttggctgcg ctacaggtca cccatctttc gttatgtcaa tgtcattcac aaaccagaca   1260

ctcgctcagc tcgacctcta cgaaaagaga ggaaatctcg agaagaaggt ttacacactt   1320

ccgaagcatc tcgatgaaga agtcgctcgc ctccacctcg gatctctcga tgtccacctt   1380

acaaagctta cacagaagca ggctgactac atcaacgttc cagttgaggg tccttacaag   1440

tctgatgctt accgttatta a                                             1461


<210> SEQ ID NO 2
<211> LENGTH: 33
<212> TYPE: DNA
<213> ORGANISM: Artificial Sequence
<220> FEATURE:
<223> OTHER INFORMATION: Upstream primer

<400> SEQUENCE: 2

ttttggatcc gcttgcaaat cacctgctgg tgc                                  33


<210> SEQ ID NO 3
<211> LENGTH: 24
<212> TYPE: DNA
<213> ORGANISM: Artificial Sequence
<220> FEATURE:
<223> OTHER INFORMATION: Downstream pprimer

<400> SEQUENCE: 3

ttttctgcag ggggagctat cgct                                            24


<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4

catcatcatc atcatcacgc ttgcaaatca cctactgg                             38


<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5

ctacgaatgg caataattcc taggtacgta                                      30


<210> SEQ ID NO 6
<211> LENGTH: 1461
<212> TYPE: DNA
<213> ORGANISM: Homo sapiens (nucleotide sequence of SAHH - wild type)

<400> SEQUENCE: 6

atggcttgca aatcacctgc tggtgctcca ttcgagtaca gaattgccga catcaacctc     60

catgttctcg gccgtaagga acttaccctt gctgagaagg aaatgccagg tcttatggtt    120
```

-continued

```
cttcgtgagc gttattccgc ttctaagcca ttgaagggtg tcagaatctc tggttccctc    180

cacatgacag tccagacagc ggtccttatt gagacactca cagctcttgg tgctgatgtc    240

agatgggctt cctgcaacat cttctctaca caagatacag ccgctgctgc tatcgttgtc    300

ggcccaacag gcacaccaga gaagccagcc ggtatcccag tcttcgcctg gaagggcgaa    360

acactcccag aatactggga gaacacatac cgcgctctca catggccaga tggtcaaggc    420

ccacagcagg ttgtcgatga tggtggtgat gctacactcc tcatctccaa gggcttcgaa    480

ttcgaaacag ccggtgctgt cccagagcca acagaagctg acaacctcga ataccgctgc    540

gttcttgcta cactcaagca ggtcttcaac caagacaaga accactggca cacagttgct    600

gccggcatga acggtgtttc cgaagagaca acaacaggtg tccaccgcct ctaccagctc    660

gagaaggagg gcaaactcct cttcccagcc atcaacgtca acgacgctgt tacaaagtcc    720

aagttcgata acatctacgg ctgtcgccac tcccttatcg atggtatcaa ccgtgcttcc    780

gatgtcatga tcggcggcaa gacagctctc gtcatgggtt acggcgatgt cgggaagggc    840

tgcgctcaat ccctccgtgg ccaaggcgct cgcgttatca tcacagaact cgaccctatc    900

tgcgctctcc aggctgtcat ggaaggctac caggtccgcc gcatcgagga agtcgtcaag    960

gatgtcgata tcttcgttac atgcacagga aactgcgata tcatctctgt tgacatgatg   1020

gcccagatga aggataaggc tattgtcggt aacatcggcc acttcgataa cgaaattgat   1080

acagatggcc tcatgaaata cccaggcatc aagcacatcc caatcaagcc agaatacgac   1140

atgtgggaat tcccagatgg ccacgctatc ctccttcttg ctgagggccg ccttcttaac   1200

cttggttgcg ctacaggtca cccatctttc gttatgtcaa tgtcattcac aaaccagaca   1260

ctcgctcagc tcgacctcta cgaaaagaga ggaaatctcg agatgaaggt ttacacactt   1320

ccgaagcatc tcgatgaaga agtcgttcgc ctccacctcg gatctctcga tgtccacctt   1380

acaaagctta cacagaagca ggctgactac atcaacgttc cagttgaggg tccttacaag   1440

tctgatgctt accgttatta a                                              1461
```

<210> SEQ ID NO 7
<211> LENGTH: 486
<212> TYPE: PRT
<213> ORGANISM: Homo sapiens

<400> SEQUENCE: 7

```
Met Ala Cys Lys Ser Pro Thr Gly Ala Pro Phe Glu Tyr Arg Ile Ala
 1               5                  10                  15

Asp Ile Asn Leu His Val Leu Gly Arg Lys Glu Leu Thr Leu Ala Glu
            20                  25                  30

Lys Glu Met Pro Gly Leu Met Val Leu Arg Glu Arg Tyr Ser Ala Ser
        35                  40                  45

Lys Pro Leu Lys Gly Val Arg Ile Ser Gly Ser Leu His Met Thr Val
    50                  55                  60

Gln Thr Ala Val Leu Ile Glu Thr Leu Thr Ala Leu Gly Ala Asp Val
65                  70                  75                  80

Arg Trp Ala Ser Cys Asn Ile Phe Ser Thr Gln Asp Thr Ala Ala Ala
                85                  90                  95

Ala Ile Val Val Gly Pro Thr Gly Thr Pro Glu Lys Pro Ala Gly Ile
            100                 105                 110

Pro Val Phe Ala Trp Lys Gly Glu Thr Leu Pro Glu Tyr Trp Glu Asn
        115                 120                 125
```

-continued

```
Thr Tyr Arg Ala Leu Thr Trp Pro Asp Gly Gln Gly Pro Gln Gln Val
    130                 135                 140

Val Asp Asp Gly Gly Asp Ala Thr Leu Leu Ile Ser Lys Gly Phe Glu
145                 150                 155                 160

Phe Glu Thr Ala Gly Ala Val Pro Glu Pro Thr Glu Ala Asp Asn Leu
                165                 170                 175

Glu Tyr Arg Cys Val Leu Ala Thr Leu Lys Gln Val Phe Asn Gln Asp
            180                 185                 190

Lys Asn His Trp His Thr Val Ala Ala Gly Met Asn Gly Val Ser Glu
        195                 200                 205

Glu Thr Thr Thr Gly Val His Arg Leu Tyr Gln Leu Glu Lys Glu Gly
    210                 215                 220

Lys Leu Leu Phe Pro Ala Ile Asn Val Asn Asp Ala Val Thr Lys Ser
225                 230                 235                 240

Lys Phe Asp Asn Ile Tyr Gly Cys Arg His Ser Leu Ile Asp Gly Ile
                245                 250                 255

Asn Arg Ala Ser Asp Val Met Ile Gly Gly Lys Thr Ala Leu Val Met
            260                 265                 270

Gly Tyr Gly Asp Val Gly Lys Gly Cys Ala Gln Ser Leu Arg Gly Gln
        275                 280                 285

Gly Ala Arg Val Ile Ile Thr Glu Leu Asp Pro Ile Cys Ala Leu Gln
    290                 295                 300

Ala Ala Met Glu Gly Tyr Gln Val Arg Arg Ile Glu Glu Val Val Lys
305                 310                 315                 320

Asp Val Asp Ile Phe Val Thr Cys Thr Gly Asn Cys Asp Ile Ile Ser
                325                 330                 335

Val Asp Met Met Ala Gln Met Lys Asp Lys Ala Ile Val Gly Asn Ile
            340                 345                 350

Gly His Phe Asp Asn Glu Ile Asp Thr Asp Gly Leu Met Lys Tyr Pro
        355                 360                 365

Gly Ile Lys His Ile Pro Ile Lys Pro Glu Tyr Asp Met Trp Glu Phe
    370                 375                 380

Pro Asp Gly His Ala Ile Leu Leu Leu Ala Glu Gly Arg Leu Leu Asn
385                 390                 395                 400

Leu Gly Cys Ala Thr Gly His Pro Ser Phe Val Met Ser Met Ser Phe
                405                 410                 415

Thr Asn Gln Thr Leu Ala Gln Leu Asp Leu Tyr Glu Lys Arg Gly Asn
            420                 425                 430

Leu Glu Lys Lys Val Tyr Thr Leu Pro Lys His Leu Asp Glu Glu Val
        435                 440                 445

Ala Arg Leu His Leu Gly Ser Leu Asp Val His Leu Thr Lys Leu Thr
    450                 455                 460

Gln Lys Gln Ala Asp Tyr Ile Asn Val Pro Val Glu Gly Pro Tyr Lys
465                 470                 475                 480

Ser Asp Ala Tyr Arg Tyr
                485
```